United States Patent
Veldman et al.

(10) Patent No.: US 8,760,649 B1
(45) Date of Patent: Jun. 24, 2014

(54) MODEL-BASED METROLOGY USING TESSELATION-BASED DISCRETIZATION

(75) Inventors: Andrei Veldman, Santa Clara, CA (US); John J. Hench, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1314 days.

(21) Appl. No.: 12/074,761

(22) Filed: Mar. 5, 2008

Related U.S. Application Data

(60) Provisional application No. 61/062,787, filed on Jan. 28, 2008.

(51) Int. Cl.
*G01N 21/00* (2006.01)
*G01N 15/02* (2006.01)
*G01N 15/14* (2006.01)
*G01N 21/53* (2006.01)

(52) U.S. Cl.
CPC ........ *G01N 15/0205* (2013.01); *G01N 15/1459* (2013.01); *G01N 21/53* (2013.01)
USPC ............................ 356/337; 356/364; 356/369

(58) Field of Classification Search
CPC .......... G01N 15/0205; G01N 15/1459; G01N 21/29; G01N 2015/1486; G01N 21/53; G01N 21/21; G01N 21/211; G01N 21/23; G01N 2021/213; G01J 4/04; G01J 4/00; G01B 11/0641
USPC .......................................... 356/364–369, 337
See application file for complete search history.

(56) References Cited

U.S. PATENT DOCUMENTS

| | | | |
|---|---|---|---|
| 6,281,027 B1 | 8/2001 | Wei et al. | |
| 6,509,199 B2 | 1/2003 | Wei | |
| 6,577,384 B2 | 6/2003 | Wei et al. | |
| 6,826,385 B2 | 11/2004 | Kujala | |
| 6,900,892 B2 * | 5/2005 | Shchegrov et al. | 356/369 |
| 7,031,848 B2 * | 4/2006 | Opsal et al. | 702/27 |
| 7,049,156 B2 | 5/2006 | Kueny | |
| 7,099,005 B1 * | 8/2006 | Fabrikant et al. | 356/369 |
| 7,116,333 B1 * | 10/2006 | Peercy | 345/582 |
| 7,158,239 B2 * | 1/2007 | Hazart | 356/601 |
| 7,321,433 B2 * | 1/2008 | Larsen et al. | 356/601 |
| 7,330,279 B2 * | 2/2008 | Vuong et al. | 356/625 |
| 7,505,153 B2 * | 3/2009 | Vuong et al. | 356/625 |
| 7,511,830 B2 * | 3/2009 | Fabrikant et al. | 356/601 |
| 2002/0012123 A1 | 1/2002 | Wei et al. | |
| 2002/0045284 A1 | 4/2002 | Wei et al. | |
| 2003/0214654 A1 | 11/2003 | Wei et al. | |
| 2004/0185582 A1 | 9/2004 | Kueny | |
| 2005/0057748 A1 | 3/2005 | Vuong et al. | |
| 2005/0192914 A1 | 9/2005 | Drege et al. | |
| 2005/0232511 A1 * | 10/2005 | Ziou et al. | 382/276 |
| 2008/0007739 A1 | 1/2008 | Vuong et al. | |
| 2008/0007740 A1 | 1/2008 | Vuong et al. | |
| 2008/0009081 A1 | 1/2008 | Madriaga et al. | |

* cited by examiner

*Primary Examiner* — Tarifur Chowdhury
*Assistant Examiner* — Isiaka Akanbi
(74) *Attorney, Agent, or Firm* — Okamoto & Benedicto LLP

(57) ABSTRACT

A novel technique for model-based metrology. A geometry of structure to be measured on a surface of a substrate is received. A tessellation of the geometry of the structure is produced. The tessellation is used to determine a vertical discretization and a horizontal discretization so as to generate a discrete model for the geometry, and scatterometry computations are performed using the discrete model. Other embodiments, aspects and features are also disclosed.

22 Claims, 17 Drawing Sheets

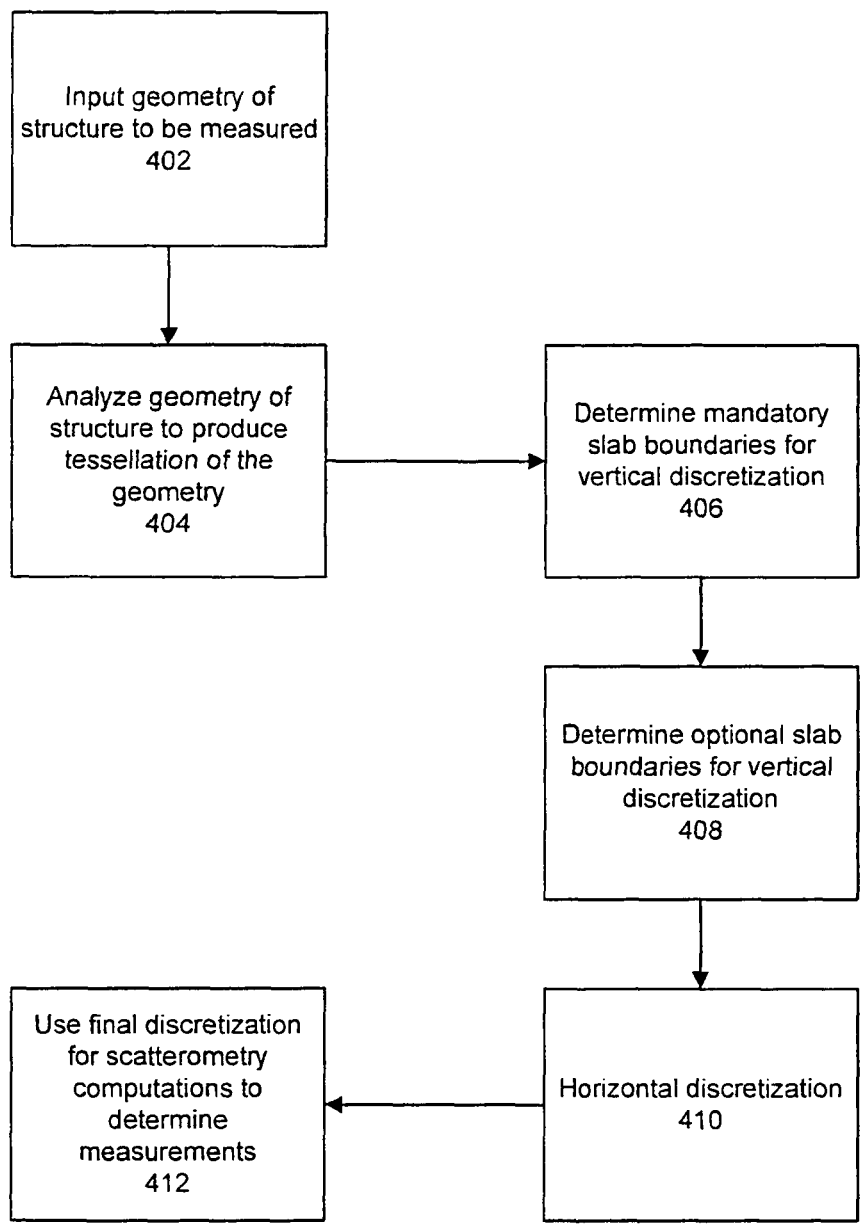
FIG. 4         400

MODEL-BASED METROLOGY USING TESSELATION-BASED DISCRETIZATION

CROSS-REFERENCE TO RELATED APPLICATIONS

The present disclosure claims the benefit of U.S. provisional patent application No. 61/062,787, entitled "Model-Based Metrology Using Tesselation-Based Discretization," filed Jan. 28, 2008 by Andrei Veldman and John Hench, the disclosure of which is hereby incorporated by reference.

BACKGROUND OF THE INVENTION

1. Technical Field

The present disclosure relates to apparatus and methods for inspecting and analyzing semiconductor wafers and other substrates using scatterometry and related techniques.

2. Description of the Background Art

Scatterometry refers to an optical technique that analyzes diffraction to deduce structural details of a diffracting sample. The diffracting sample is generally a periodic structure, that is, a grating. Scatterometry may be used to measure or analyze two-dimensional structures (line gratings), as well as three-dimensional structures (such as periodic patterns of mesas or vias on a substrate).

Metrology methods using scatterometry rely on being able to accurately model the features that are being measured, calculate the light diffraction properties of the feature, and find a match between the calculated and measured values. In other words, theoretical model is defined for each physical structure to be analyzed, and calculated data using the model is then compared or analyzed against measured data. Typically, the measured data are related to the light diffraction efficiency as a function of wavelength, incidence angle, or both.

It is desirable to improve inspection and metrology for the manufacture of semiconductors and other substrates.

SUMMARY

The present application discloses a novel technique for model-based metrology. A geometry of structure to be measured on a surface of a substrate is received. A tessellation of the geometry of the structure is produced. The tessellation is used to determine a vertical discretization and a horizontal discretization so as to generate a discrete model for the geometry, and scatterometry computations are performed using the discrete model.

Other embodiments, aspects, and features are also disclosed.

BRIEF DESCRIPTION OF THE DRAWINGS

FIG. 4 is a flow chart of a method of using tessellation-based discretization for model-based metrology in accordance with an embodiment of the invention.

DETAILED DESCRIPTION

Scatterometry Measurements

Figure 1:
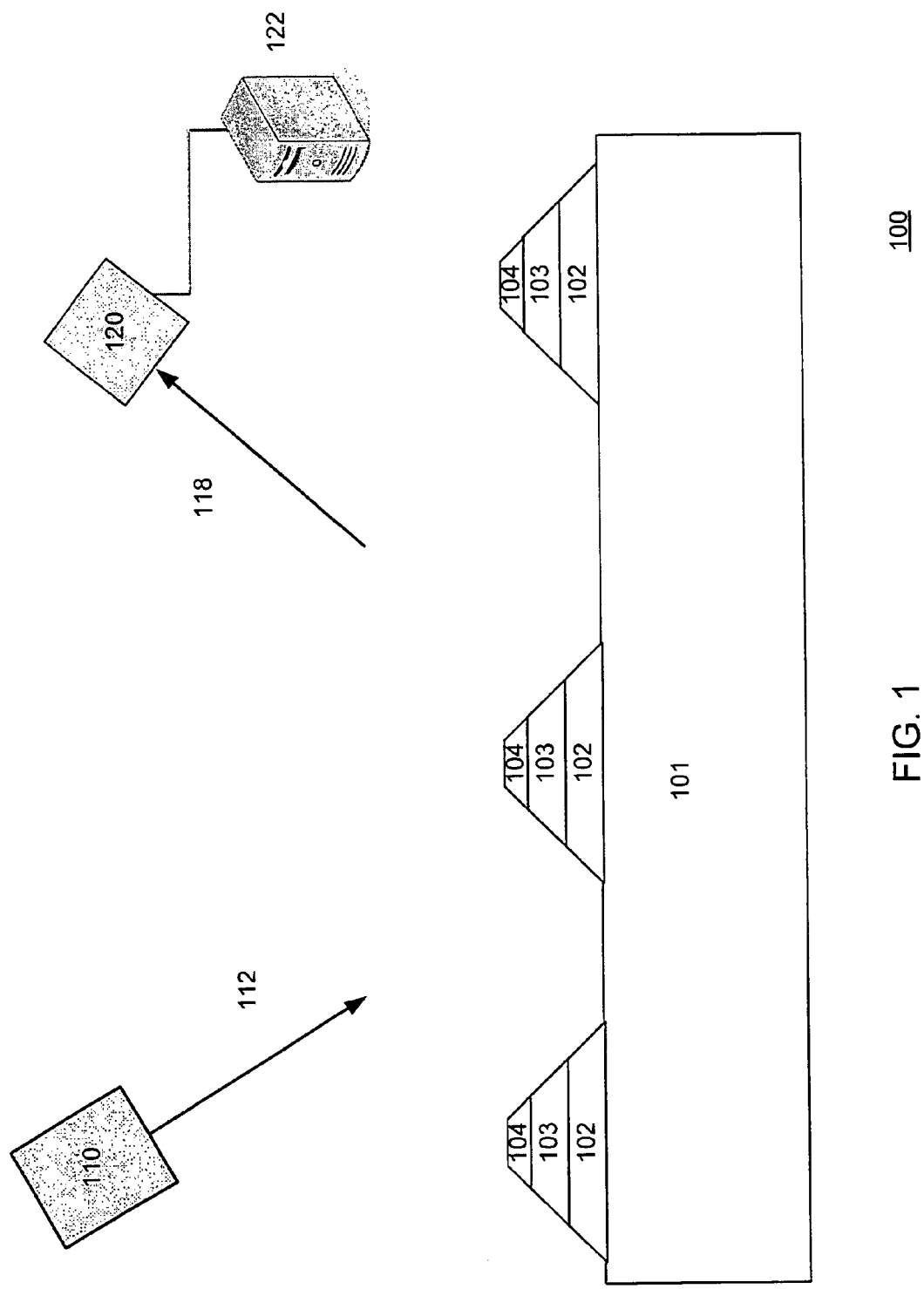
FIG. 1 is a schematic diagram depicting a scatterometry configuration applied to a semiconductor wafer with devices formed thereon and a simple example of discretized features on the wafer.

FIG. 1 is a schematic diagram depicting a scatterometry configuration 100 applied to a semiconductor wafer 101 with devices formed thereon and a simple example of discretized features on the wafer. More particularly, FIG. 1 shows in cross-sectional view an example target substrate 101 upon which has been fabricated an array of features. In this case, pyramidal mesas have been formed on the surface of the substrate. Here, the pyramid mesas may be discretized into slabs, for example, the three illustrated slabs 102, 103, and 104 per mesa.

As further shown in FIG. 1, a typical scatterometry configuration includes an illumination source 110 that produces a monochromatic or polychromatic light beam 112. The light beam may be focused by an illumination lens system (not illustrated) to illuminate a spot or region on the surface of a target substrate 101. The light is diffracted or scattered by features in the illuminated region. The diffracted or scattered light 118 is focused by a collection lens system (not illustrated) to a detector 120.

The detection of the diffracted light provides diffraction data which may then be processed by a data processing system 122. The data processing system 122 may include various components, such as a processor for executing computer-readable instructions, a data storage system for storing the computer-readable instructions and other data, memory for holding the computer-readable instructions and other data, input and output interfaces, and a bus or other communications system which interconnects the components. The data processing system 122 may be configured to perform computations and other processing steps used to make measurements of feature dimensions using scatterometry.

Further details regarding an example scatterometer system is given, for example, in U.S. Pat. No. 6,483,580, "Spectroscopic Scatterometer System,"Yiping Xu and Ibrahim Abdulhalim, assignee KLA-Tencor Technologies Corporation. The disclosure of U.S. Pat. No. 6,483,580 is hereby incorporated by reference.

Previous Discretization Methods for Model-Based Metrology

Previous discretization methods for model-based metrology are based on analytical or approximate geometrical solutions for a very limited range of three-dimensional (3D) shapes for which such solutions are available, typically conical or pyramidal holes or posts. When other shapes are modeled, the vertical discretization is either the same as for a cone or simply consists of uniform slabs. Occasionally, the vertical discretization is not done automatically, being left to a human operator. The typical horizontal discretization for complex geometries (anything different from an ellipse or a parallelogram) is based on sampling the materials on a regular grid of points in the unit cell.

Applicants have identified several disadvantages of previous discretization methods. These disadvantages are: inaccuracy, inefficiency in speed and computer memory usage, non-smooth behavior, difficulty in assigning one material to each sampling point and, of particular relevance, being tailored to specific (and simple) geometries.

What is meant by non-smooth behavior is that, when one changes the geometrical parameters describing the shape of the smooth model by a very small amount, the corresponding discretized version may change drastically; this behavior causes the computation of the spectrum gradient with respect to geometrical parameters to be highly inaccurate.

Regarding the horizontal discretization, even at relatively high unit cell sampling densities on the order of hundreds of points in each direction, the distance between points may still be on the order of one nanometer (1 nm), i.e. large compared to the accuracy and precision requirements. Moreover, the discrete character of sampling on a grid produces a very non-smooth computed response, especially when the material boundaries happen to be aligned with special directions of the sampling grid. In other words, a geometrical parameter change can move the boundary across many points of the grid, in which case the computed scatterometry spectra will show a jump which is just an artifact of the sampling without any basis in reality.

Regarding the vertical discretization, the disadvantage of having a non-optimal discretization for general geometries is that the rigorous coupled-wave analysis (RCWA) computation results are inaccurate and/or prohibitively expensive computation-wise. The results are inaccurate for those slabs where the approximation is poor (thus making the overall results inaccurate). The RCWA computation may be prohibitively expensive if the number of slabs is increased until all the slabs are sufficiently accurate approximations.

Finally, the accuracy/efficiency behavior of the old methods depends strongly on how different is the geometry to discretize from the one for which the discretization was developed. Therefore, the discretization algorithm and code need to be modified when new geometry requirements occur.

Figures 2A, 2B:
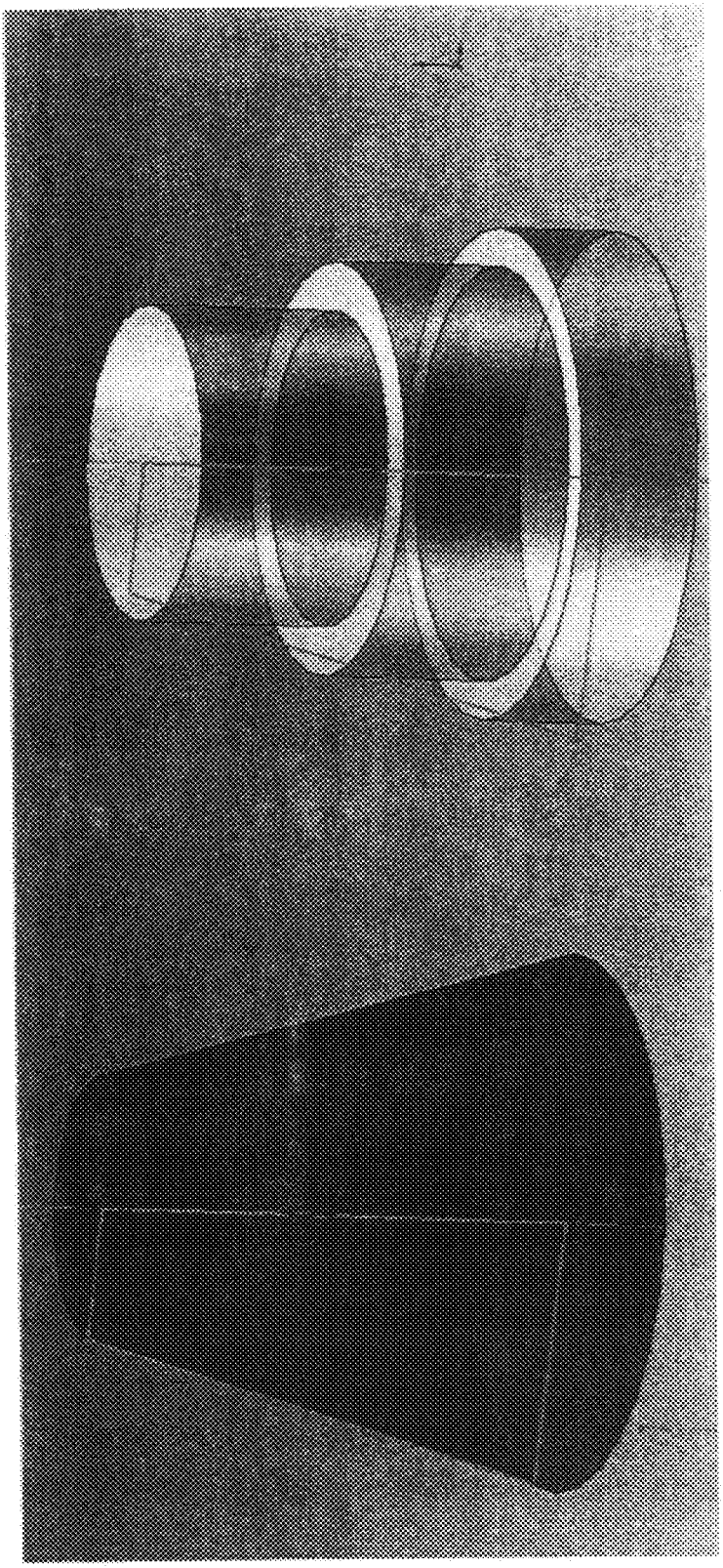
FIG. 2A is a perspective diagram of an example conical frustum.
FIG. 2B is a perspective diagram of an example discretization of the conical frustum into three slabs.

The purpose of discretization is to find a collection of discrete slabs that approximate a given structure. FIGS. 2A and 2B show an example discretization of a conical frustum using three slabs. FIG. 2A is a perspective diagram of the conical frustum. FIG. 2B is a perspective diagram of an example discretization of the conical frustum into three slabs.

Figures 3A, 3B, 3C:
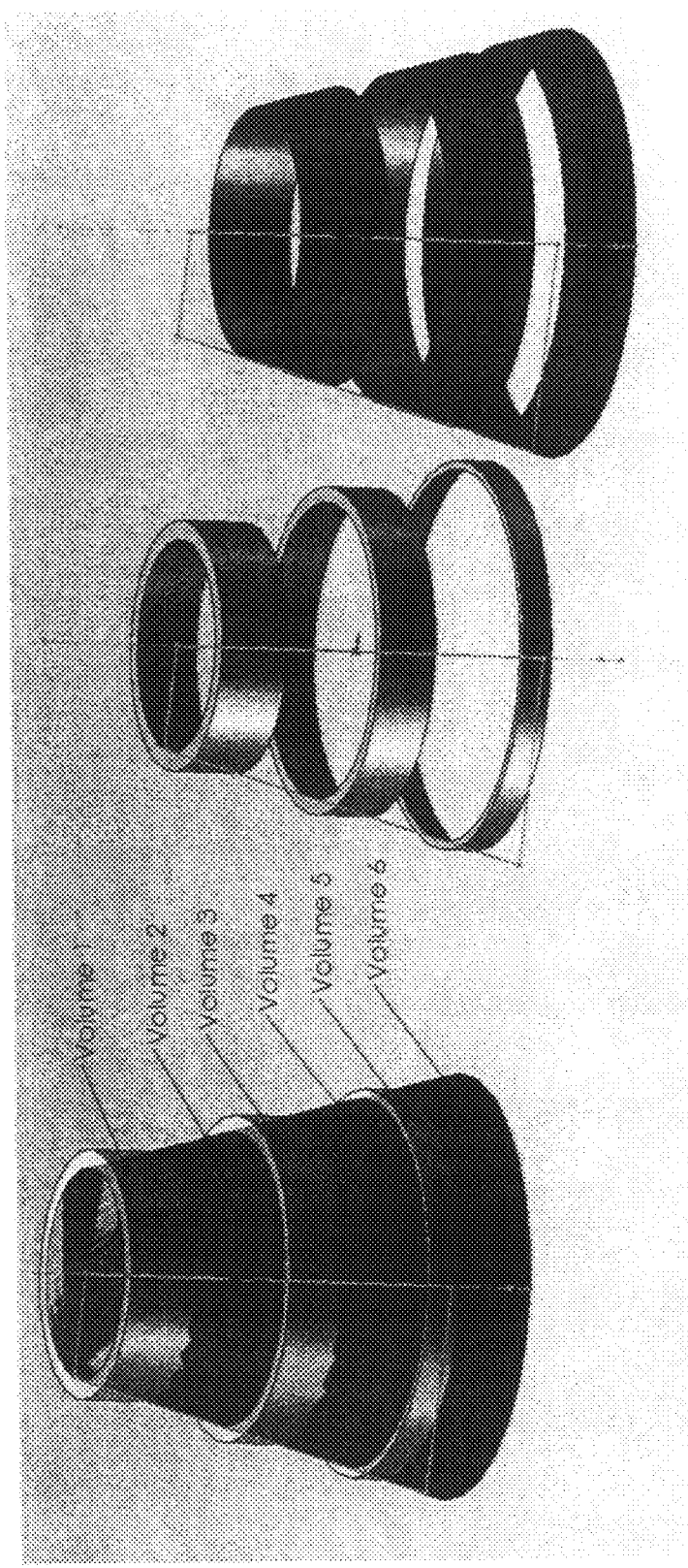
FIG. 3A is a perspective diagram showing six error volumes between the conical frustum of FIG. 2A and the three-slab discretization of FIG. 2B.
FIG. 3B is a perspective diagram showing the first, third and fifth error volumes due to the volume of the three slabs in FIG. 2B being larger than the conical frustum of FIG. 2A.
FIG. 3C is a perspective diagram showing the second, fourth, and sixth error volumes due to the volume of the three slabs in FIG. 2B being smaller than the conical frustum of FIG. 2A.

FIGS. 3A, 3B and 3C illustrate the accuracy (or inaccuracy) of the example discretization of FIGS. 2A and 2B. FIG. 3A is a perspective diagram showing six error volumes between the conical frustum of FIG. 2A and the three-slab discretization of FIG. 2B. FIG. 3B is a perspective diagram showing the first, third and fifth error volumes due to the volume of the three slabs in FIG. 2B being larger than the conical frustum of FIG. 2A. FIG. 3C is a perspective diagram showing the second, fourth, and sixth error volumes due to the volume of the three slabs in FIG. 2B being smaller than the conical frustum of FIG. 2A.

Tesselation-Based Discretization for Model-Based Metrology

It is desirable to improve over prior discretization methods for model-based metrology. In particular, the present application discloses an improvement where the discretization technique works equally well or nearly equally well for arbitrary geometries or at least a very wide variety of geometries. In addition, the discretization technique disclosed herein provides smooth results in a fast and accurate manner.

The present application discloses tessellation-based discretization for calculating scatterometry measurements. The tessellation-based discretization involves geometrically analyzing the triangles and polygons produced by the tessellation of the geometry of the features. This technique is advantageously more general so as to be able to work with arbitrary geometries and is capable of more closely modeling the features on a semiconductor wafer in comparison to the conventional approach.

FIG. 4 is a flow chart of a method 400 of using tessellation-based discretization for model-based metrology in accordance with an embodiment of the invention. In a first step (block 402), the geometry of the structure to be measured is input. As discussed above, as an advantage of this tessellation-based technique, the geometry may be arbitrary or nearly arbitrary.

In accordance with an embodiment of the invention, a geometric modeling engine (GME) is then utilized to analyze the geometry of the structure to produce a tessellation of the geometry (block 404). Such a GME has the general capability of rendering an arbitrary structure and efficiently tessellating the bodies appearing in the structure. The GME also has the capability to render curves produced by intersecting the bodies with horizontal planes, irrespective of the shape of the structure, at a controllable degree of accuracy. Such a GME may be implemented using a GME of the type used in mechanical engineering drawing software and is commercially available.

Figure 12A:
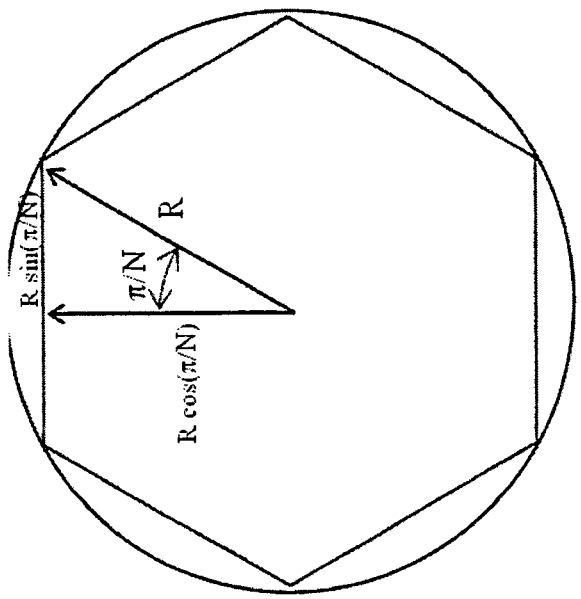
FIG. 12A is an example diagram showing polygonal vertices of a tessellation on a continuous curve in accordance with an embodiment of the invention.
Figure 12B:
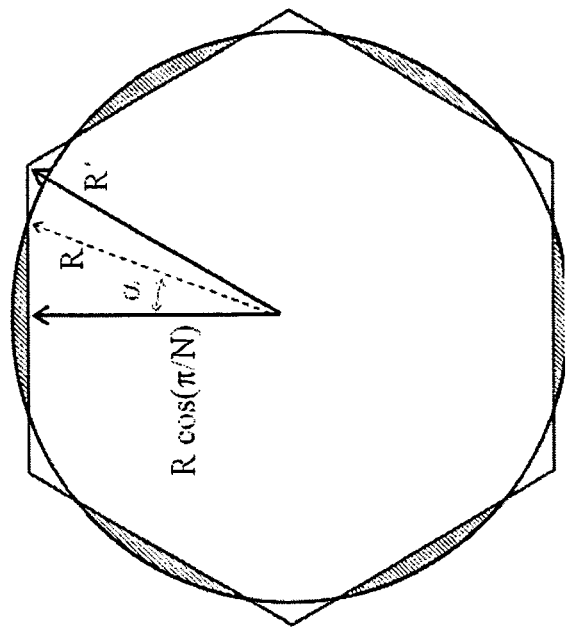
FIG. 12B is an example diagram showing polygonal vertices of a tessellation outside a continuous curve in accordance with an embodiment of the invention.

In further accordance with an embodiment of the invention, the tessellation of a three-dimensional (3D) body (per block 404) produces a tiling of all the faces of that body by triangles with no gaps or overlaps, and the tessellation of a curve produces a polygonal line with its vertices lying on that curve, such as shown in FIG. 12A. Alternatively, if a higher volumetric accuracy is necessary or desired, the polygonal vertices may be moved outside the curvature of the continuous curves, as shown in FIG. 12B.

Figure 5A:
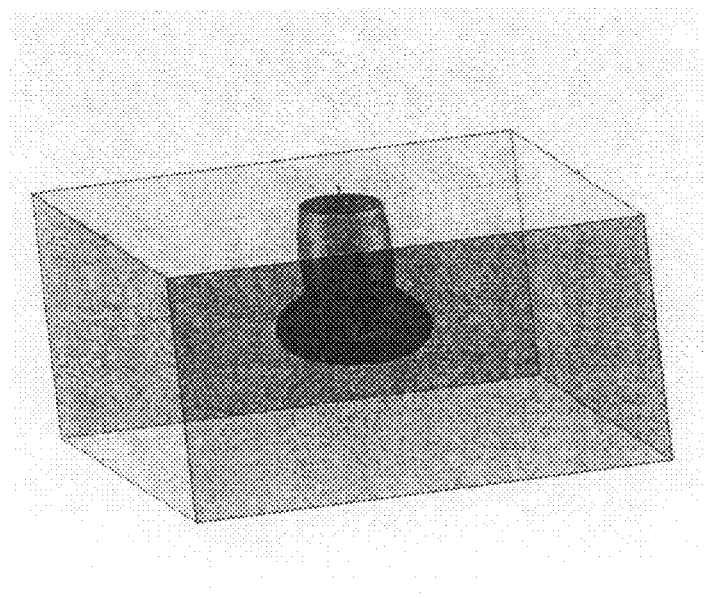
FIG. 5A is perspective diagram showing an example three-dimensional geometry comprising an opening in a material layer.
Figure 5B:
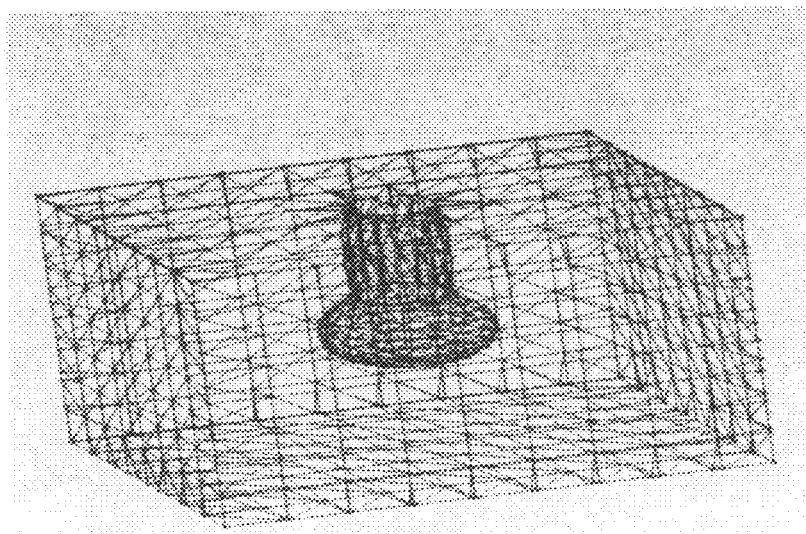
FIG. 5B is a perspective diagram showing an example tessellation determined by analyzing the geometry of FIG. 5A in accordance with an embodiment of the invention.

An example of a tessellation of a 3D body (per block 404) is now discussed in relation to FIGS. 5A and 5B. FIG. 5A is a perspective diagram showing a three-dimensional geometry comprising an opening in a material layer (such as an etched hole in a semiconductor layer). As shown in FIG. 5A, the opening is somewhat cylindrical near the surface and has a enlarged (bulbous) portion deeper in the material. FIG. 5B depicts the tessellation of the opening in the material layer in accordance with an embodiment of the invention. The tessellation of FIG. 5B is determined by analyzing the geometry of FIG. 5A in accordance with an embodiment of the invention.

After the tessellation (per block 404), mandatory slab boundaries may be determined for the purpose of vertical discretization (block 406). In accordance with an embodiment of the invention, vertices located at stationary points of the tessellation of the faces are determined, and the mandatory slab boundaries are placed at all such vertices located at stationary points.

Figure 6A:
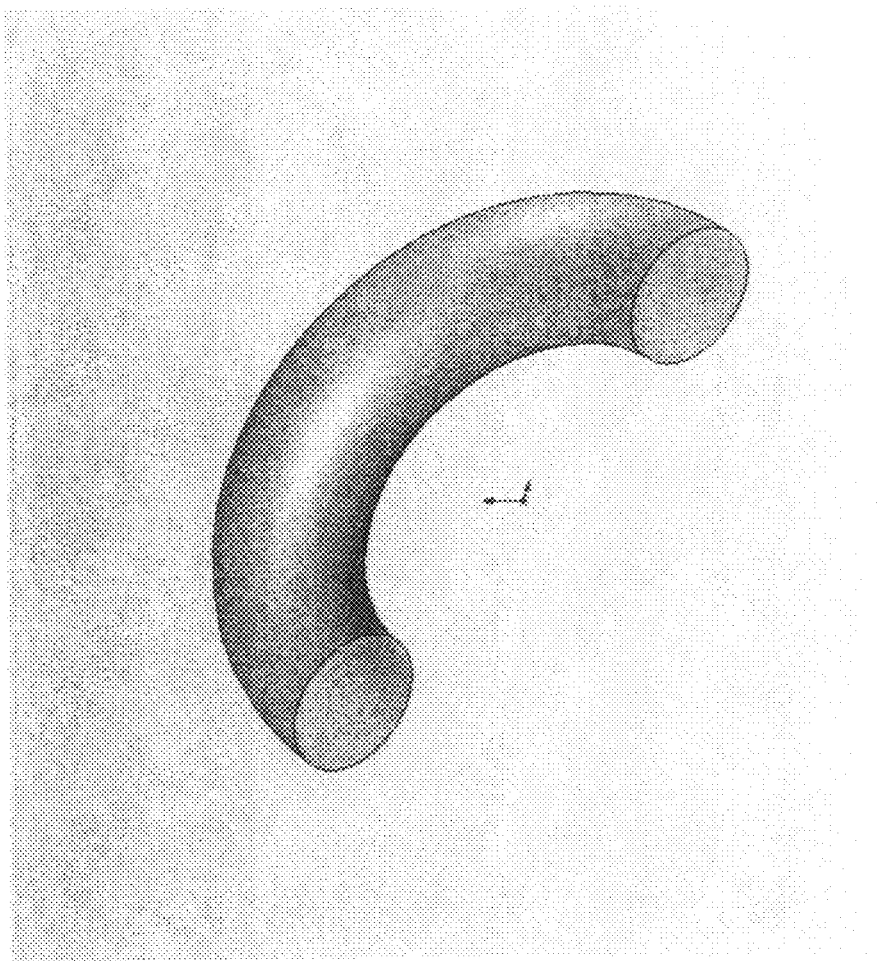
FIG. 6A is a perspective diagram of an example torus-shaped geometry.
Figure 6B:
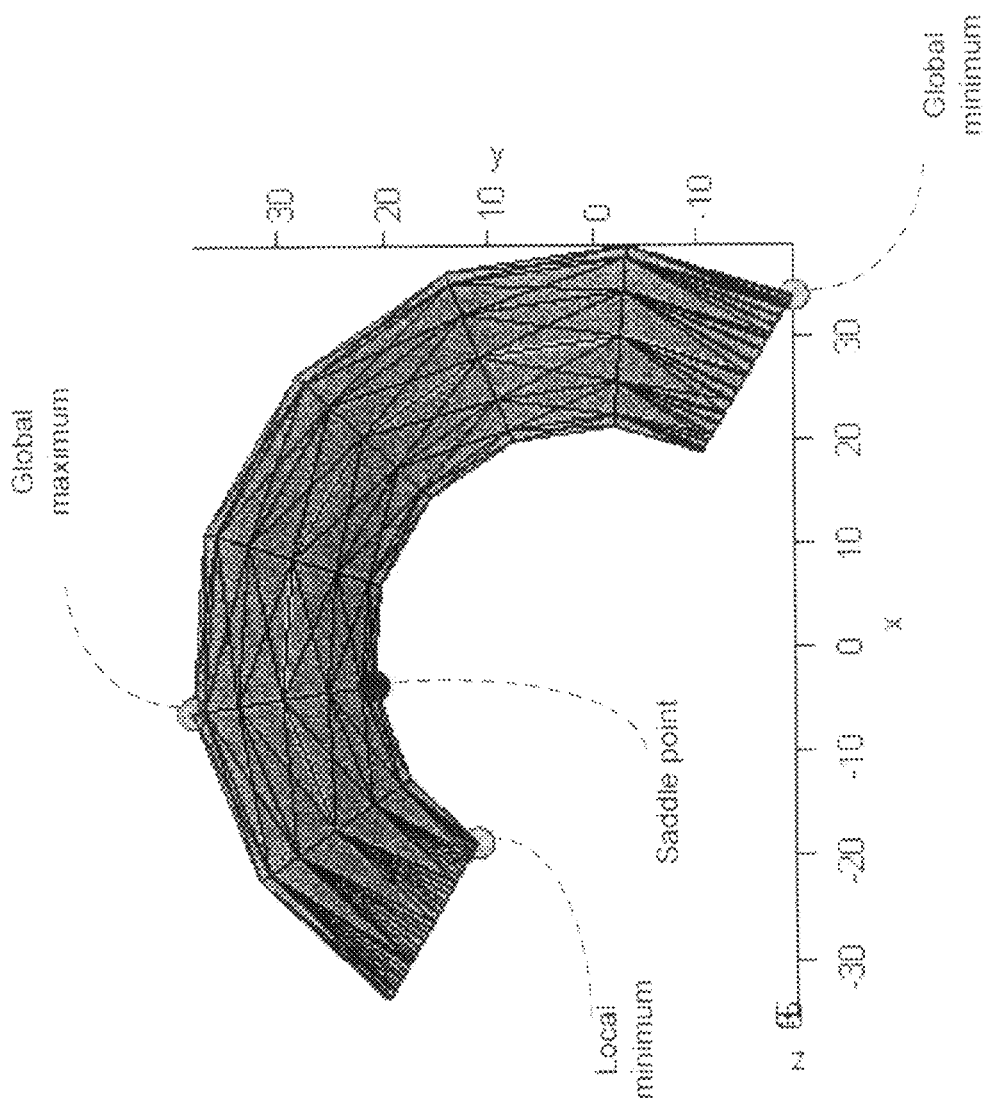
FIG. 6B is a diagram showing a discretization of the example torus-shaped geometry and further showing various vertices located at stationary points in accordance with an embodiment of the invention.

An example showing tessellation vertices at stationary points is now discussed in relation to FIGS. 6A and 6B. FIG. 6A is a perspective diagram of an example torus-shaped geometry. FIG. 6B is a diagram showing a discretization of the example torus-shaped geometry and further showing various vertices located at stationary points in accordance with an embodiment of the invention. Such stationary points are minima (global or local), maxima (global or local), or saddle points of various orders of the tessellated faces. In the particular example shown in FIG. 6B, vertices are shown located at a global maximum, a global minimum, a local minimum, and a saddle point as examples of vertices located at stationary points.

In accordance with an embodiment of the invention, these vertices at stationary points may be found using the following method. For each vertex of the tessellation, to determine whether the vertex is a stationary point, the tessellation fins connected to the vertex are traversed in topological order. In other words, the order in which the fins are connected by triangular facets. As the fins are traversed, the number of times the horizontal plane passing through the vertex is crossed is counted. This count is called the number of horizontal crossings. Due to the periodicity of the problem (since the starting and end points of the traversal are the same), the number of horizontal crossings is even.

Figure 7A:
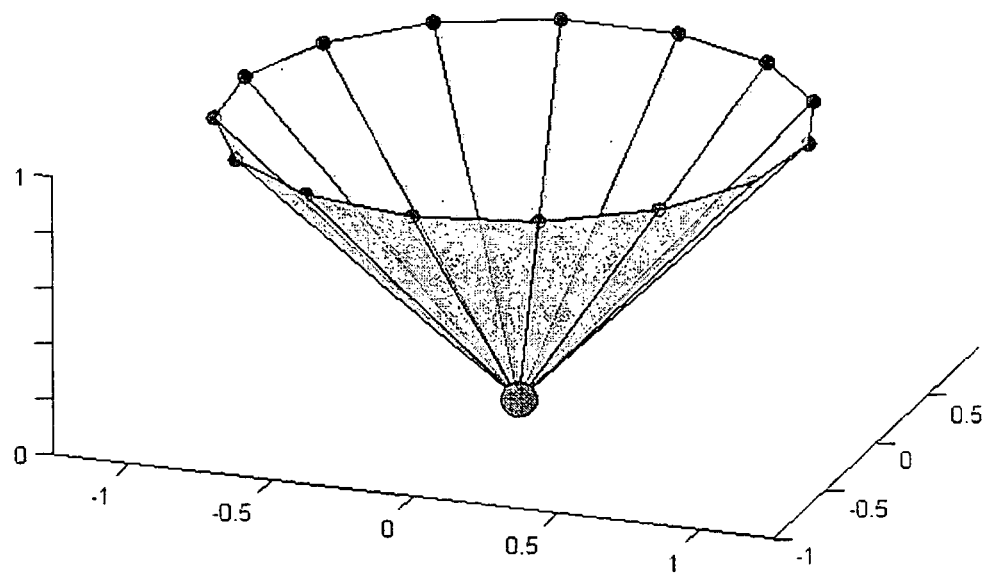
FIG. 7A is a perspective diagram illustrating a minimum point of a tessellation in accordance with an embodiment of the invention.
Figure 7B:
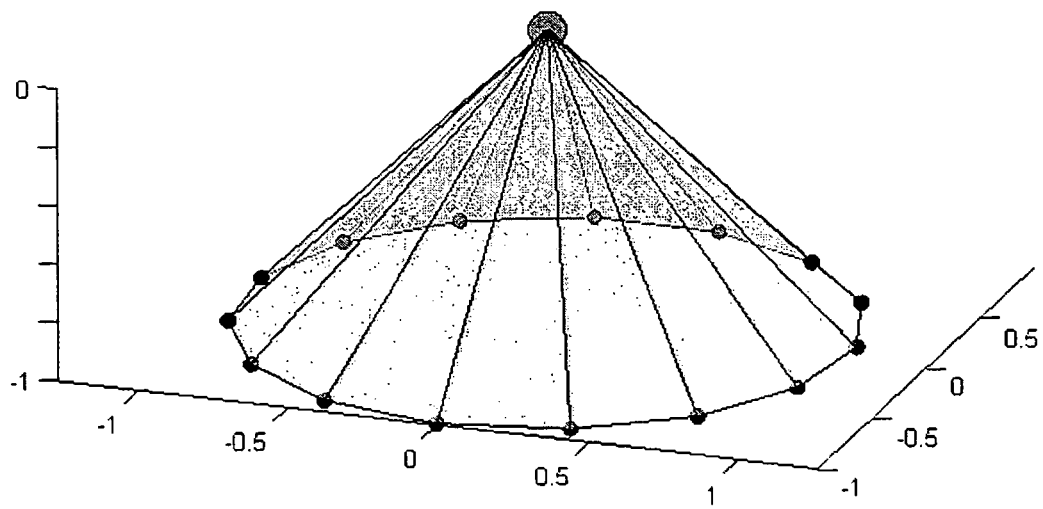
FIG. 7B is a perspective diagram illustrating a maximum point of a tessellation in accordance with an embodiment of the invention.

If the number of horizontal crossings is zero, then the vertex is at a minimum or maximum point of the tessellation. FIG. 7A is a perspective diagram illustrating a minimum point of a tessellation in accordance with an embodiment of the invention. FIG. 7B is a perspective diagram illustrating a maximum point of a tessellation in accordance with an embodiment of the invention.

Figure 7C:
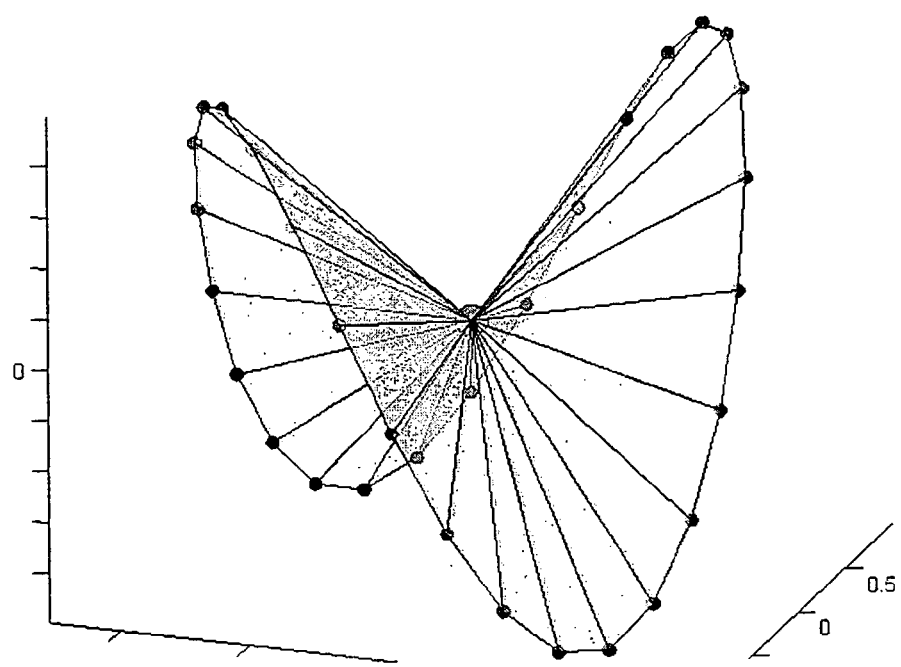
FIG. 7C is a perspective diagram illustrating a first type of saddle point of a tessellation in accordance with an embodiment of the invention.
Figure 7D:
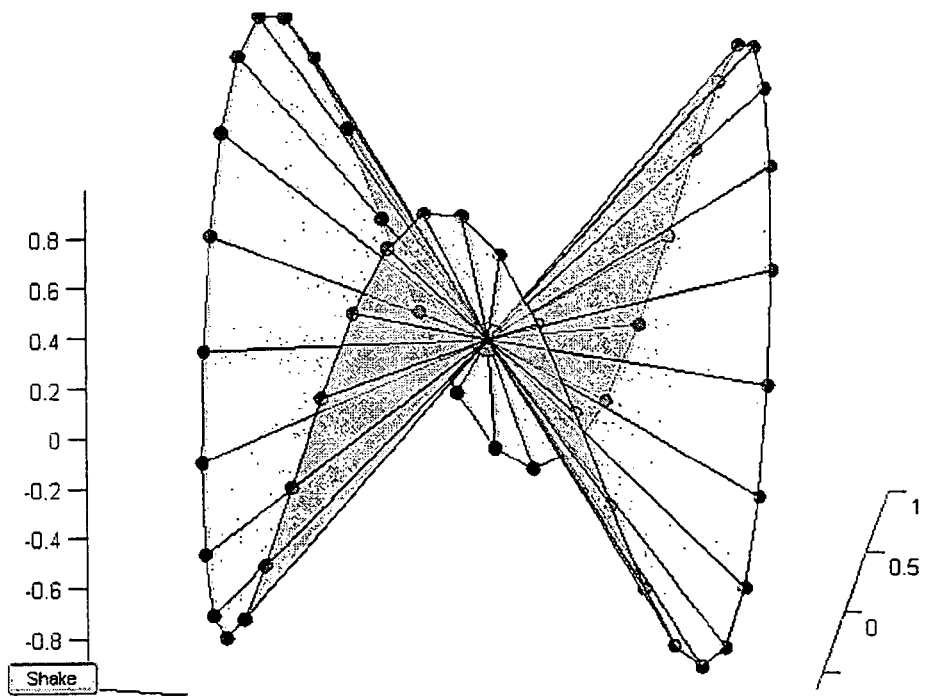
FIG. 7D is a perspective diagram illustrating a second type of saddle point of a tessellation in accordance with an embodiment of the invention.

If the number of horizontal crossings is an even number which is four or larger, then the vertex is at a minimum or maximum point of the tessellation. FIG. 7C is a perspective diagram illustrating a saddle point of a tessellation where the number of horizontal crossing points is four in accordance with an embodiment of the invention. FIG. 7D is a perspective diagram illustrating a saddle point of a tessellation where the number of horizontal crossing points is six in accordance with an embodiment of the invention.

Figure 7E:
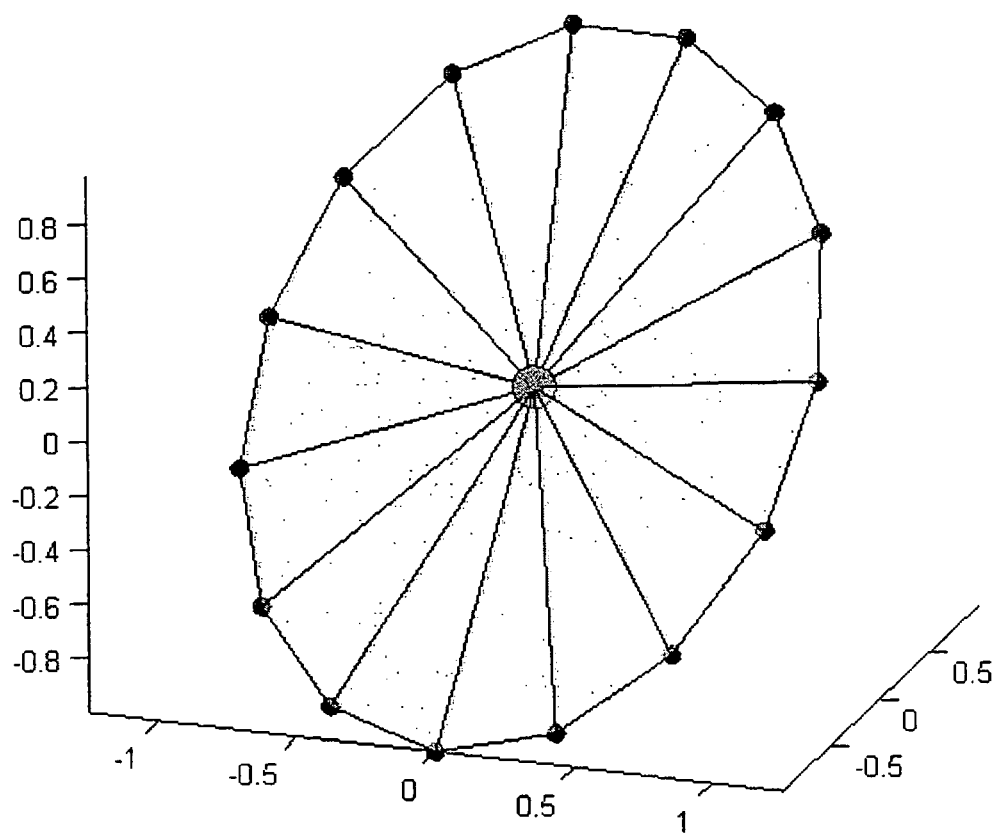
FIG. 7E is a perspective diagram illustrating a non-stationary point of a tessellation in accordance with an embodiment of the invention.

If the number of horizontal crossings is two, then the vertex is at a non-stationary point of the tessellation. FIG. 7E is a perspective diagram illustrating a non-stationary point of a tessellation in accordance with an embodiment of the invention.

Thus, only if the number of horizontal crossings is two, then the vertex is at a non-stationary point such that there is no mandatory slab boundary at that vertex. If the number of horizontal crossings is 0, 4, 6, 8, or greater even numbers, then the vertex is at a stationary point such that a mandatory (horizontal) slab boundary is placed at that vertex for purposes of vertical discretization.

After the mandatory slab boundaries are placed (per block 406), optional slab boundaries may be determined for the purpose of vertical discretization (block 408). In accordance with an embodiment of the invention, between every two mandatory slab boundaries found, additional slab boundaries may be determined and used if the volumetric error $\Delta V$ between the slab with vertical boundaries between materials and the inclined material walls of the continuous geometry is larger than a predetermined threshold volume $\Delta V_0$. An example of a volumetric error is shown by the ring-shaped bodies in FIGS. 3B and 3C.

Figure 8A:
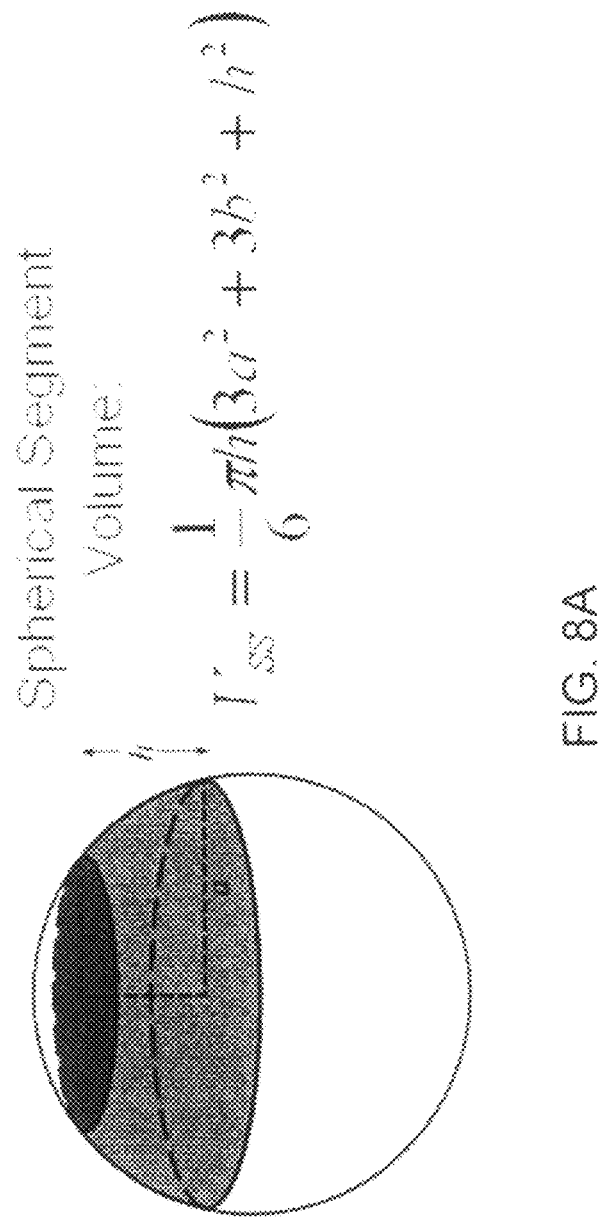
FIG. 8A is a perspective diagram showing a spherical segment volume in accordance with an embodiment of the invention.
Figure 8B:
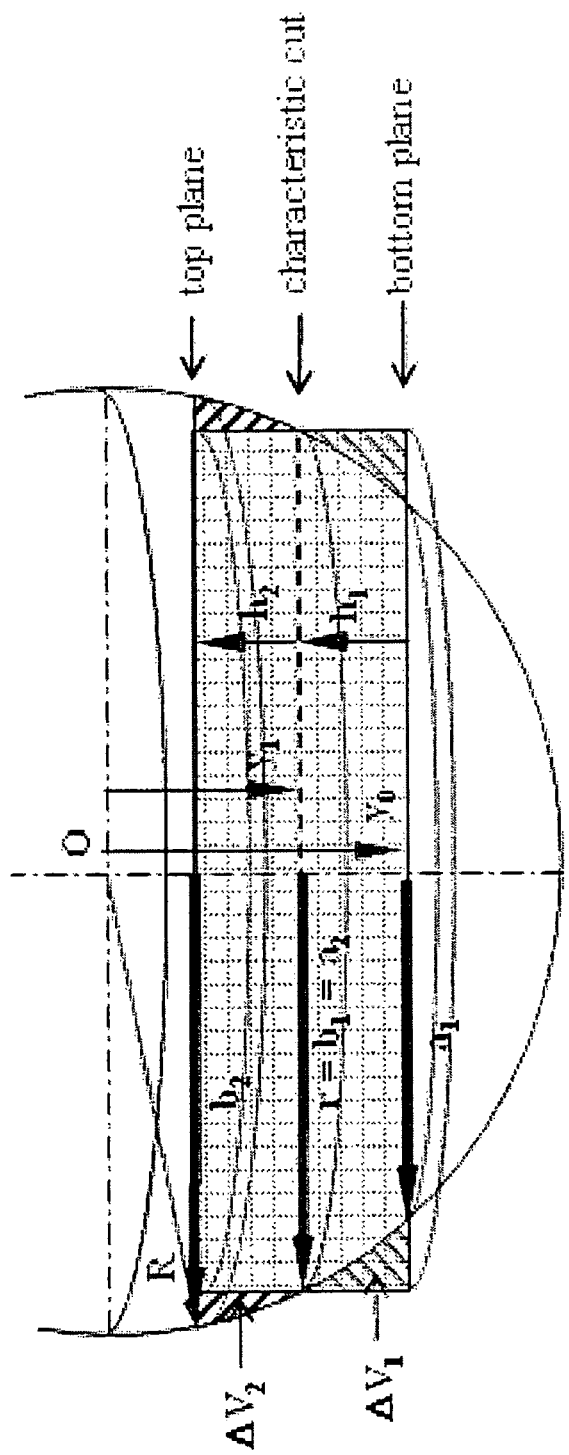
FIG. 8B is a perspective diagram showing error volume between a spherical segment volume and a slab in accordance with an embodiment of the invention.

For very simple continuous geometries, there may be analytical solutions to determining the volumetric errors and optional slab boundaries. For example, for a continuous geometry which is a sphere, FIG. 8A shows the spherical segment volume, and FIG. 8B shows the volumetric error between a disc-shaped slab and a spherical segment. Per FIG. 8B, the volumetric error is $\Delta V = \Delta V_1 + \Delta V_2$. The height of the characteristic cut above the bottom plane may be determined by solving the following equation: $\Delta V_1 = -(2\pi/3)h_1^3 - \pi y_1 h_1^2$. The height of the slab top above the characteristic cut may be determined by solving the following equation: $-\Delta V_2 = -(\pi/3)h_2^3 - \pi y_1 h_2^2$.

Figure 8C:
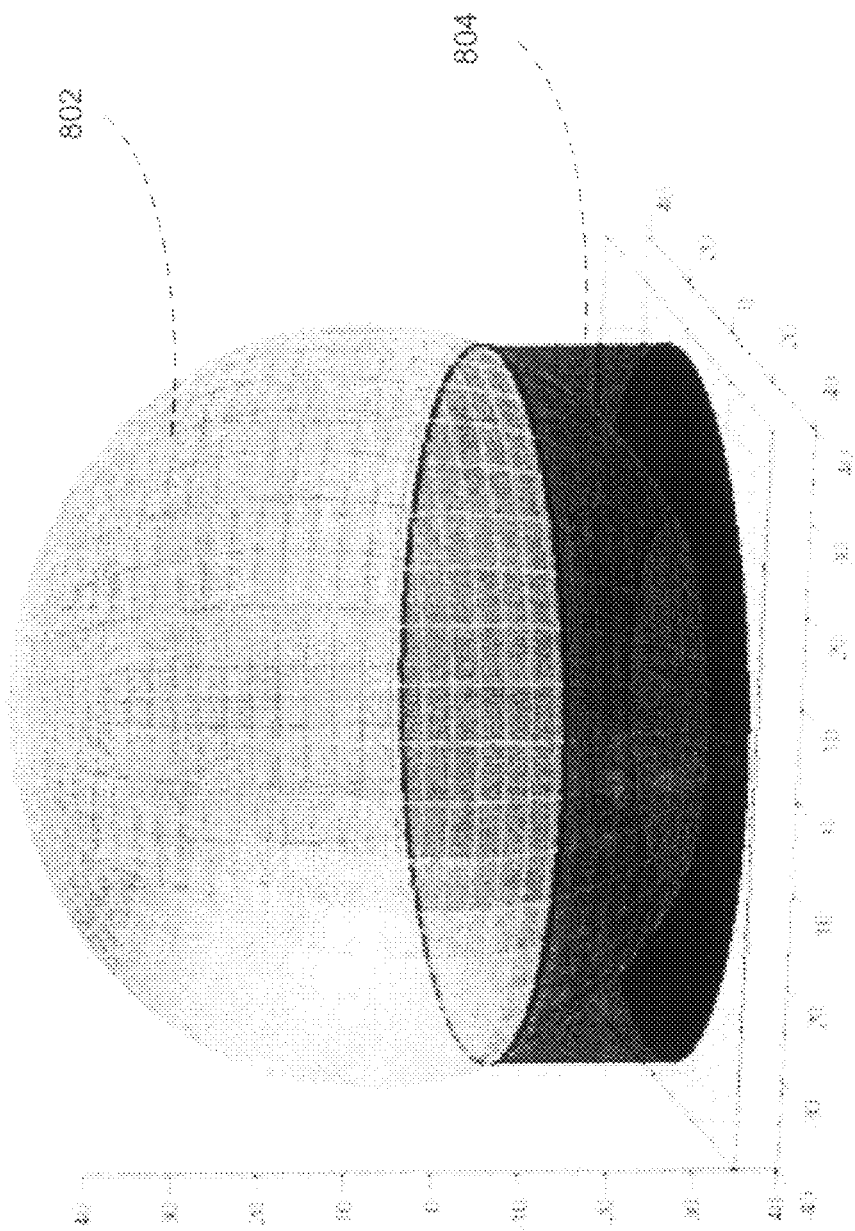
FIG. 8C is a perspective diagram depicts a sphere and an approximate or quasi volumetric error for that sphere in accordance with an embodiment of the invention.
Figure 9:
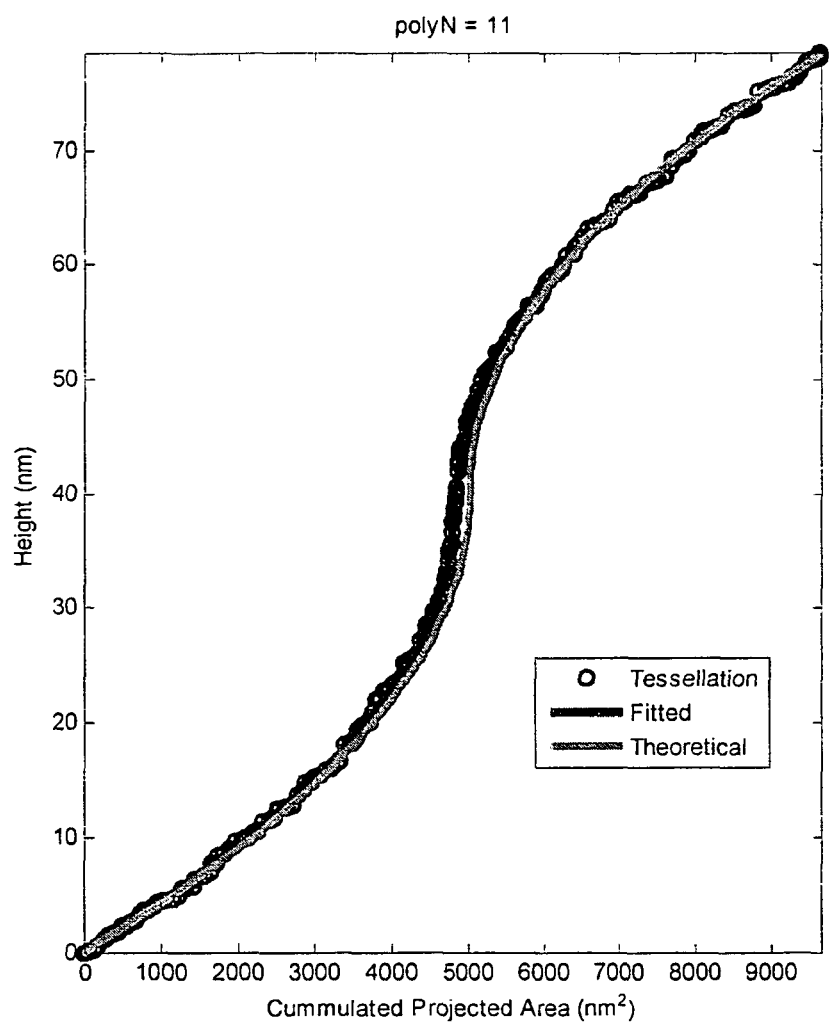
FIG. 9 is a graph showing a polynomial fit to the cumulated projected area of tessellation facets in accordance with an embodiment of the invention.

For an arbitrary geometry that is not solved analytically, an approximate method may be used for estimating the volumetric error between the slab and the continuous geometry. The approximate method considers the approximate or "quasi" volumetric error to be half the absolute value of the projection of the lateral area of all the material interfaces in the structure onto a horizontal plane multiplied by the height. For example, the quasi volumetric error is approximately half the volume of the body 804 shown in FIG. 8C for the spherical segment 802 shown. In practice, for an arbitrary geometry, the method may be implemented by calculating the cumulative area of the projection of the triangular facets of the tessellation onto a horizontal plane as a function of the height of the center of these facets, and fit a polynomial curve to it, as depicted in FIG. 9. FIG. 9 is a graph showing a polynomial fit to the cumulated projected area of tessellation facets in accordance with an embodiment of the invention. If extended regions with perfectly or nearly perfectly vertical walls occur, then these regions may be eliminated from the fit because polynomials inherently model flat regions poorly.

In other implementations, other fit functions may be used to represent the cumulative projected area. For example, separate polynomials may be used, one for each vertical region between two mandatory slab boundaries. As another example, functions other than polynomials, such as rational functions may be used to capture sharp edges better than polynomials. An alternative embodiment may involve fitting the volume directly, instead of fitting the projected area and multiplying by height.

Figure 10:
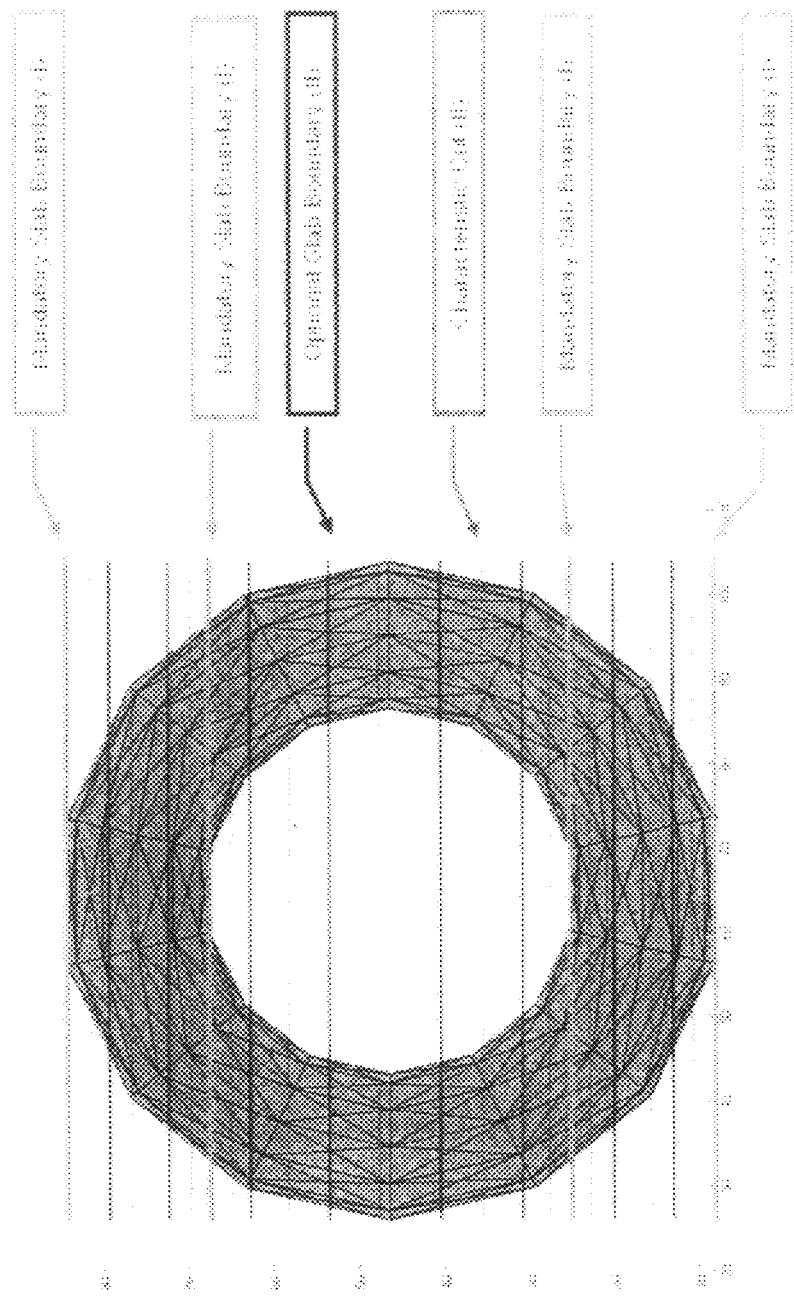
FIG. 10 is a schematic diagram showing an example of mandatory and optional slab boundaries determined for a torus-shaped feature in accordance with an embodiment of the invention.

Example results of the steps of blocks 406 and 408 are shown in FIG. 10 for a torus-shaped geometry. FIG. 10 is a schematic diagram showing an example of mandatory and optional slab boundaries determined for a torus-shaped geometry in accordance with an embodiment of the invention. Characteristic cuts are also shown. Note that while the preferred embodiment uses only one characteristic cut per slab, other embodiments may use two or more characteristic cuts per slab.

In accordance with an embodiment of the invention, horizontal discretization is performed (block 410) after the vertical discretization (blocks 406 and 408). In one implementation, the intersections of all the bodies in the structure with horizontal planes located at the height of the characteristic cuts are computed. The result of these intersection operations is a set of trimmed sheet bodies. The trimming curves that bound these bodies are extracted, and these trimming curves are tessellated. The tessellation may be performed using the same GME as discussed above. This produces a set of closed polygonal lines, representing a contiguous region in the slab inside which there is a single material.

Figure 11:
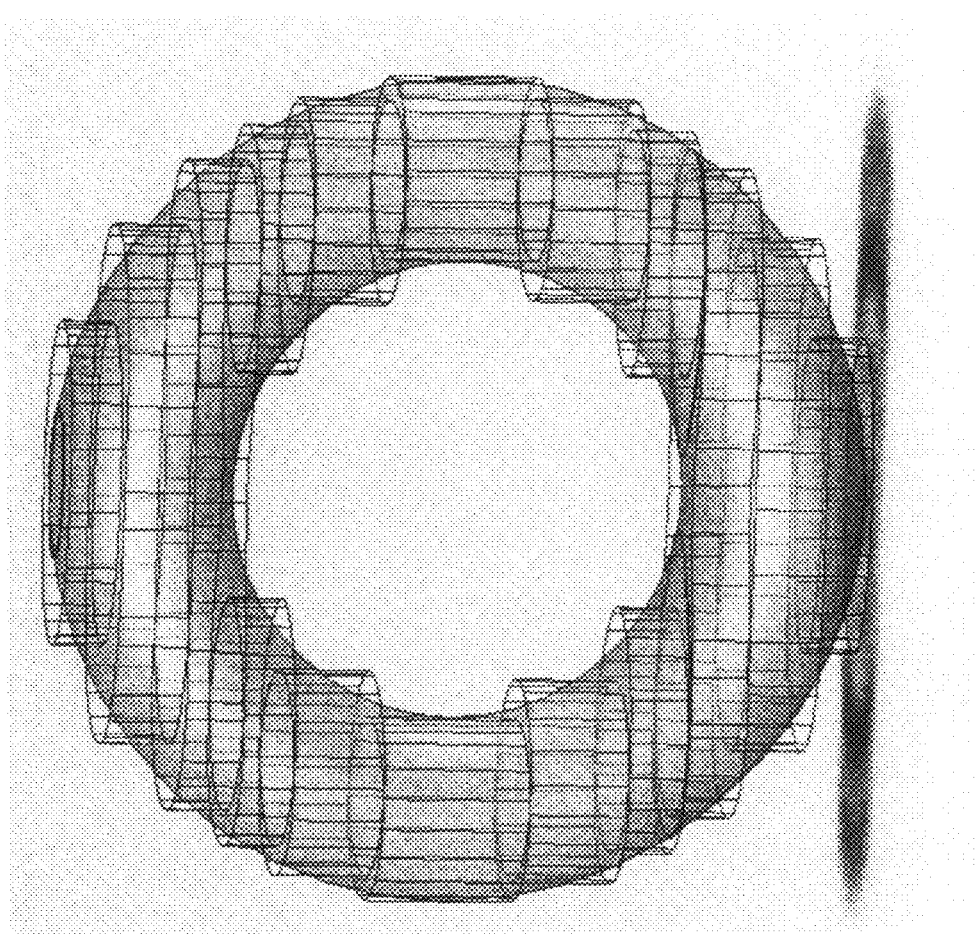
FIG. 11 is a perspective diagram of a final discretization result in accordance with an embodiment of the invention.

Thus, after completion of the vertical and horizontal discretizations, the continuous geometry is replaced by a slabbed (also known as "staircase approximation") geometry, which has vertical material boundaries within each slab. FIG. 11 is a perspective diagram of a final discretization result for the torus-shaped geometry in accordance with an embodiment of the invention. The final discretization results may then be used for scatterometry computations to determine measurements (block 412).

While the above-discussed technique uses intersections with horizontal planes, an alternative technique may use intersections with vertical planes. Similarly, while the above-discussed technique projects areas onto horizontal planes, an alternative technique may project areas onto vertical planes Advantageously, the above-described method has generality such that RCWA scatterometry computations may be performed for structures with arbitrary geometries. The method may process any shape that may be converted by a GME into tessellations of bodies, faces and curves. A brand new geometry may be advantageously processed without updating or changing the method.

In addition, a ΔV accuracy criterion may be specified and applied on a standardized basis to any shape, allowing for a straightforward and simple way to control the accuracy of the scatterometry calculation.

Further, this method avoids discontinuities due to discretization artifacts so as to produce smooth discretization results. This allows the computation of high quality geometrical and spectral derivatives.

Yet another advantage is that our prototype version of this method indicates that the computational cost is relatively low for this method, allowing for high-speed computations.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of model-based metrology, the method comprising:
   receiving geometry of structure to be measured on surface of substrate;
   producing a tessellation of the geometry of the structure;
   using the tessellation to determine a vertical discretization and a horizontal discretization so as to generate a discrete model for the geometry, wherein the tessellation comprises a polygonal structure which approximates the geometry, and a curve is tessellated by replacing the curve with a polygonal line; and
   performing scatterometry computations using the discrete model to measure of one or more features of the structure on the surface of the substrate and storing results of said measurement,
   wherein a face is tessellated with triangular tiles.

2. The method of claim 1, wherein the tessellation is produced using a geometric modeling engine.

3. The method of claim 2, wherein the method is useable for model-based metrology of an arbitrary geometry which is not from a set of predetermined geometries.

4. The method of claim 1, wherein the vertical discretization is performed prior to the horizontal discretization.

5. The method of claim 4, wherein mandatory horizontal slab boundaries are determined in performing the vertical discretization.

6. The method of claim 5, wherein the mandatory horizontal slab boundaries are located at vertices of the tessellation which are stationary points.

7. The method of claim 6, wherein further horizontal slab boundaries are determined between the mandatory horizontal slab boundaries.

8. The method of claim 7, wherein the further horizontal slab boundaries are determined if a volumetric error is larger than a predetermined threshold volume.

9. A method of model-based metrology, the method comprising:
   receiving geometry of structure to be measured on surface of substrate;
   producing a tessellation of the geometry of the structure;
   using the tessellation to determine a vertical discretization and a horizontal discretization so as to generate a discrete model for the geometry, wherein the tessellation comprises a polygonal structure which approximates the geometry, and a curve is tessellated by replacing the curve with a polygonal line; and
   performing scatterometry computations using the discrete model to measure of one or more features of the structure on the surface of the substrate and storing results of said measurement,
   wherein the horizontal discretization forms trimming curves based on an intersection of characteristic cut planes with the geometry.

10. The method of claim 9, wherein the trimming curves are tessellated.

11. The method of claim 9, wherein the vertical discretization is performed prior to the horizontal discretization.

12. An apparatus for model-based metrology, the apparatus comprising:
  a target substrate with a surface structure repeated thereon in an array;
  an illumination source and lens system which are configured to produce a monochromatic or polychromatic light beam and to focus the light beam onto at least a portion of the array;
  a collection lens system and detector which are configured to detect light that is diffracted or scattered by the array so as to generate diffraction data; and
  a data processing system for processing the diffraction data and for applying the model-based metrology to determine a measurement of one or more features of the surface structure from the diffraction data, wherein the model-based metrology comprises a tesselation of the surface structure, wherein the tessellation comprises a polygonal structure which approximates the geometry, and a curve is tessellated by replacing the curve with a polygonal line,
  wherein a face is tessellated with triangular tiles.

13. The apparatus of claim 12, wherein the tessellation is produced using a geometric modeling engine.

14. The apparatus of claim 13, wherein the apparatus is useable for model-based metrology of an arbitrary geometry which is not from a set of predetermined geometries.

15. The apparatus of claim 13, wherein the vertical discretization is performed prior to the horizontal discretization.

16. The apparatus of claim 12, wherein mandatory horizontal slab boundaries are determined in performing the vertical discretization.

17. The apparatus of claim 16, wherein the mandatory horizontal slab boundaries are located at vertices of the tessellation which are stationary points.

18. The apparatus of claim 17, wherein further horizontal slab boundaries are determined between the mandatory horizontal slab boundaries.

19. The apparatus of claim 18, wherein the further horizontal slab boundaries are determined if a volumetric error is larger than a predetermined threshold volume.

20. An apparatus for model-based metrology, the apparatus comprising:
  a target substrate with a surface structure repeated thereon in an array;
  an illumination source and lens system which are configured to produce a monochromatic or polychromatic light beam and to focus the light beam onto at least a portion of the array;
  a collection lens system and detector which are configured to detect light that is diffracted or scattered by the array so as to generate diffraction data; and
  a data processing system for processing the diffraction data and for applying the model-based metrology to determine a measurement of one or more features of the surface structure from the diffraction data, wherein the model-based metrology comprises a tesselation of the surface structure, wherein the tessellation comprises a polygonal structure which approximates the geometry, and a curve is tessellated by replacing the curve with a polygonal line,
  wherein the horizontal discretization forms trimming curves based on an intersection of characteristic cut planes with the geometry.

21. The apparatus of claim 20, wherein the trimming curves are tessellated.

22. The apparatus of claim 20, wherein the vertical discretization is performed prior to the horizontal discretization.

* * * * *